(12) United States Patent
Mals

(10) Patent No.: US 9,872,966 B2
(45) Date of Patent: Jan. 23, 2018

(54) GAS DELIVERY CONDUIT FOR A RESPIRATORY THERAPY SYSTEM

(71) Applicant: KONINKLIJKE PHILIPS N.V., Eindhoven (NL)

(72) Inventor: Susan Marie Mals, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 642 days.

(21) Appl. No.: 14/390,630

(22) PCT Filed: Apr. 12, 2013

(86) PCT No.: PCT/IB2013/052933
§ 371 (c)(1),
(2) Date: Oct. 3, 2014

(87) PCT Pub. No.: WO2013/156914
PCT Pub. Date: Oct. 24, 2013

(65) Prior Publication Data
US 2015/0083131 A1 Mar. 26, 2015

Related U.S. Application Data

(60) Provisional application No. 61/625,369, filed on Apr. 17, 2012.

(51) Int. Cl.
*A61M 16/08* (2006.01)
*F16L 11/02* (2006.01)
(Continued)

(52) U.S. Cl.
CPC ........ *A61M 16/0875* (2013.01); *A61M 16/04* (2013.01); *A61M 16/0622* (2014.02); *F16L 11/02* (2013.01)

(58) Field of Classification Search
CPC ...... A61M 16/08–16/0891; F16L 11/02; F16L 11/08; F16L 11/081–11/083; F16L 11/088; F16L 11/10
See application file for complete search history.

(56) References Cited

U.S. PATENT DOCUMENTS 3,109,461 A * 11/1963 Wolff ...................... F16L 11/10
138/110
5,454,061 A * 9/1995 Carlson ................... B29C 66/49
392/472
(Continued)

FOREIGN PATENT DOCUMENTS

CN 1111333 A 11/1995
GB 0557770 9/1942
(Continued)

*Primary Examiner* — Valerie L Woodward
(74) *Attorney, Agent, or Firm* — Michael W. Haas

(57) ABSTRACT

A delivery conduit (6A,6A',6B,6C) for delivering a flow of gas in a respiratory therapy system (2) includes an elongated wall member (22,34) made of a textile material, and a support member (24, 36, 36', 36", 42, 50, 58, 64, 70) extending along at least a portion of the length of the wall member. The support member engages either the inner surface or the outer surface of the wall member, and engages less than the entirety of the inner surface or the outer surface of the wall member such that a plurality of portions of the wall member are not engaged by the support member and at the plurality of portions the wall member is the only barrier to the gas within the delivery conduit.

5 Claims, 6 Drawing Sheets

(51) Int. Cl.
*A61M 16/06* (2006.01)
*A61M 16/04* (2006.01)

(56) References Cited

U.S. PATENT DOCUMENTS

| | | | |
|---|---|---|---|
| 5,573,039 A * | 11/1996 | Mang | F16L 11/12 |
| | | | 138/137 |
| 5,706,864 A | 1/1998 | Pfleger | |
| 6,044,844 A * | 4/2000 | Kwok | A61M 16/06 |
| | | | 128/205.25 |
| 9,278,184 B2 | 3/2016 | Sofranko | |
| 2002/0002976 A1* | 1/2002 | Smith | A61M 16/08 |
| | | | 128/203.16 |
| 2004/0079371 A1* | 4/2004 | Gray | A61M 16/08 |
| | | | 128/204.17 |
| 2006/0102184 A1 | 5/2006 | Kullik | |
| 2006/0108066 A1 | 5/2006 | Smith | |
| 2007/0246043 A1* | 10/2007 | Kwok | A61M 16/0666 |
| | | | 128/201.22 |
| 2008/0060649 A1* | 3/2008 | Veliss | A61M 16/06 |
| | | | 128/205.25 |
| 2008/0173305 A1* | 7/2008 | Frater | A61M 16/08 |
| | | | 128/204.26 |
| 2010/0018534 A1 | 1/2010 | Veliss | |
| 2010/0224195 A1* | 9/2010 | Henry | A61M 16/0875 |
| | | | 128/205.25 |
| 2011/0000492 A1 | 1/2011 | Veliss | |
| 2011/0016654 A1* | 1/2011 | Chudleigh | A47L 9/24 |
| | | | 15/300.1 |
| 2011/0146685 A1 | 6/2011 | Allan | |
| 2011/0197341 A1 | 8/2011 | Formica | |
| 2011/0247619 A1* | 10/2011 | Formica | F16L 11/111 |
| | | | 128/204.18 |
| 2014/0007881 A1* | 1/2014 | Rummery | A61M 16/0683 |
| | | | 128/206.21 |
| 2014/0102456 A1* | 4/2014 | Ovizinsky | A61M 16/06 |
| | | | 128/205.25 |
| 2014/0373840 A1* | 12/2014 | Graham | A61M 39/08 |
| | | | 128/203.27 |

FOREIGN PATENT DOCUMENTS

| | | |
|---|---|---|
| WO | WO2007109837 A1 | 10/2007 |
| WO | WO2009026627 A1 | 3/2009 |
| WO | WO2011051837 A1 | 5/2011 |

* cited by examiner

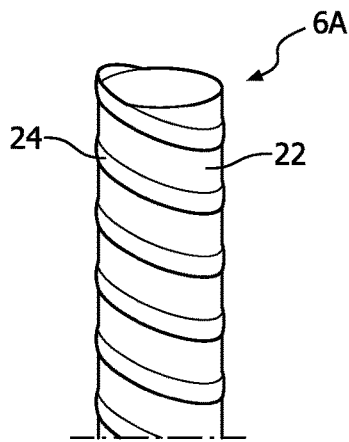 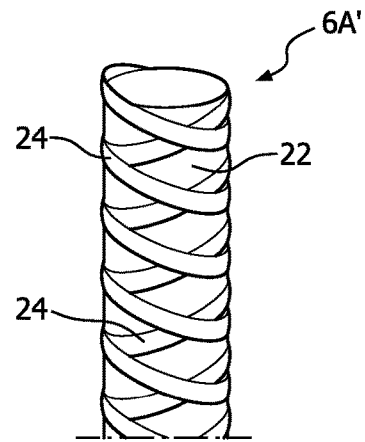
FIG. 2　　　　　FIG. 2A
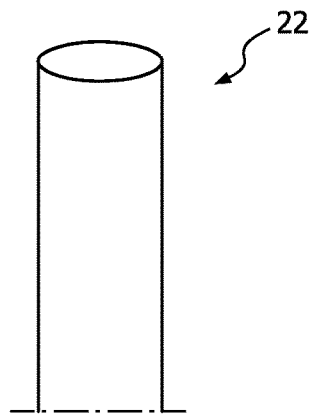
FIG. 3
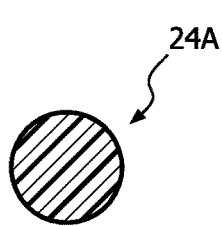 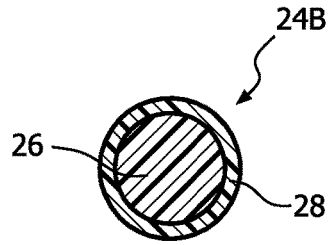 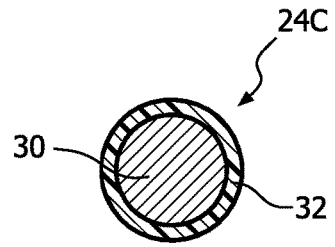
FIG. 4　　　　FIG. 5　　　　FIG. 6

GAS DELIVERY CONDUIT FOR A RESPIRATORY THERAPY SYSTEM

CROSS-REFERENCE TO RELATED APPLICATIONS

This patent application claims the priority benefit under 35 U.S.C. §371 of international patent application no. PCT/IB2013/052933, filed Apr. 12, 20132, which claims the priority benefit under 35 U.S.C. § 119(e) of U.S. Provisional Application No. 61/625,369 filed on Apr. 17, 2012, the contents of which are herein incorporated by reference.

BACKGROUND OF THE INVENTION

1. Field of the Invention

The present invention relates to respiratory therapy systems, such as non-invasive ventilation and pressure support systems, and, in particular, to a light-weight, highly flexible gas delivery conduit for such a respiratory therapy system.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

In current non-invasive ventilation and pressure support therapy systems, the gas delivery tube or conduit is typically a plastic component with an integral plastic helical support member on the exterior tube wall surface. Such plastic tubes typically look and feel industrial or medicinal in nature, since their shape is similar to large size industrially made hoses. To many users, this look and feel is not pleasing (from an aesthetic and/or tactile perspective) and may even be intimidating. This in turn may hinder usage and/or lead to issues with therapy compliance.

SUMMARY OF THE INVENTION

Accordingly, it is an object of the present invention to provide a gas delivery conduit for a respiratory therapy system that overcomes the shortcomings of conventional gas delivery conduits. This object is achieved according to one embodiment of the present invention by providing a gas delivery conduit that includes a textile wall member that provides a softer tactile feel and/or a greater visual appeal to the user.

In one embodiment, a delivery conduit for delivering a flow of gas in a respiratory therapy system is provided that includes an elongated wall member made of a textile material, and a support member extending along at least a portion of the length of the wall member. The support member engages either the inner surface or the outer surface of the wall member, and engages less than the entirety of the inner surface or the outer surface of the wall member such that a plurality of portions of the wall member are not engaged by the support member and at the plurality of portions the wall member is the only barrier to the gas within the delivery conduit. In one particular embodiment, the support member is a coil member coupled to the outer or inner surface of the textile wall member. In an alternative particular embodiment, the support member is a skeleton frame member having a spine member and a plurality of rib members provided along the spine member.

In another embodiment, a delivery conduit for delivering a flow of gas in a respiratory therapy system is provided that includes a support structure and a wall operatively coupled to the support structure such that at least a portion of the wall defines a passage adapted to carry the flow of gas, wherein the support structure and the wall are structured and arranged such that the delivery conduit has at least one of (i) a bend radius to outer diameter ratio that is greater than or equal to 1.00 mm/mm and less than or equal to 1.67 mm/mm, and (ii) a mass to length ratio that is greater than or equal to 0.03 grams/mm and less than or equal to 0.06 grams/mm.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 2 is an isometric view of a textile-based delivery conduit of the system of FIG. 1 according to one particular, exemplary embodiment;

FIG. 2A is an isometric view of a textile-based delivery conduit of the system of FIG. 1 according to an alternative particular, exemplary embodiment;

FIG. 3 is an isometric view of a textile wall member of the delivery conduit of FIG. 2;

FIGS. 4-6 are cross-sectional views of different embodiments of a coil member forming part of the delivery conduit of FIG. 2;

DETAILED DESCRIPTION OF EXEMPLARY EMBODIMENTS

Figure 1:
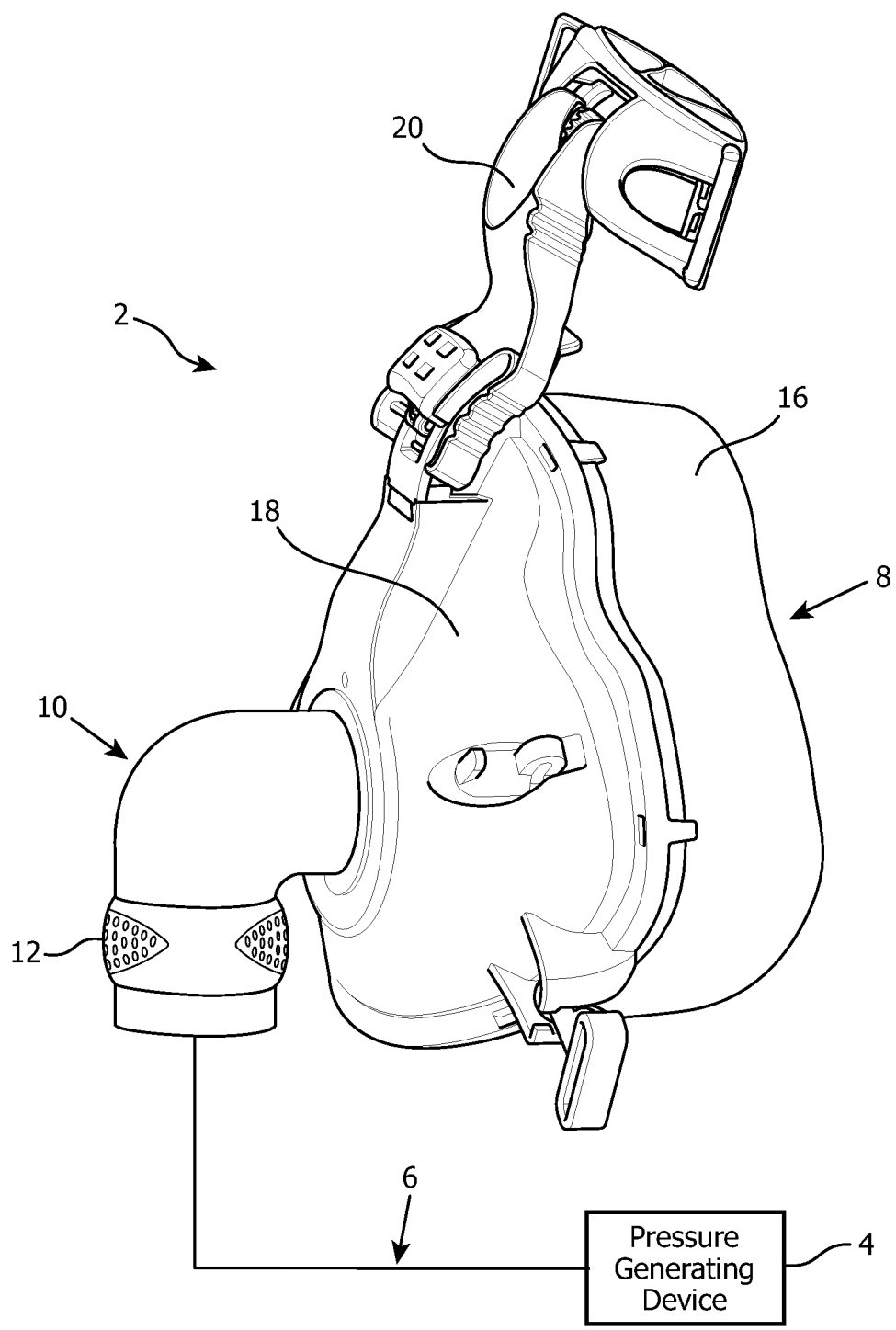
FIG. 1 is a schematic diagram of a system adapted to provide a regimen of respiratory therapy to a patient according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the word "textile" means a material consisting of a network of interlaced or otherwise entangled natural or artificial fibers made by, for example and without limitation, weaving, knitting, spreading, crocheting, or bonding (e.g., by chemical, mechanical, heat or solvent treatment) the fibers to form the network, and may include, for example, and without limitation, woven and nonwoven fabric materials.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment is generally shown in FIG. 1. System 2 includes a pressure generating device 4, a textile-based delivery conduit 6 (described in greater detail herein), a patient interface device 8, and an elbow conduit 10 having an exhaust port 12 provided therein. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the illustrated embodiment, patient interface 8 is a nasal/oral mask structured to cover the nose and mouth of the patient. However, any type of patient interface device 8, such as, without limitation, a nasal mask that covers the patient's nose, a nasal cushion having nasal prongs that are received within the patient's nares, or a full face mask that covers the patient's face, which facilitates the delivery of the flow of breathing gas to, and the removal of a flow of exhalation gas from, the airway of a patient may be used while remaining within the scope of the present invention.

In the embodiment shown in FIG. 1, patient interface 8 includes a flexible cushion 16, a rigid or semi-rigid shell 18, and a forehead support 20. Straps (not shown) of a headgear component may be attached to shell 18 and forehead support 20 to secure patient interface device 8 to the patient's head. An opening in shell 18 to which elbow conduit 10 is coupled allows the flow of breathing gas from pressure generating device 4 to be communicated to an interior space defined by shell 18 and cushion 16, and then, to the airway of a patient. The opening in shell 18 also allows the flow of exhalation gas (from the airway of such a patient) to be communicated to exhaust port 12 of elbow conduit 10 in the current embodiment.

As described in greater detail herein in connection with various particular exemplary embodiments, delivery conduit 6 is a textile-based conduit wherein, instead of having a traditional plastic tube wall for delivering gas, the tube wall of delivery conduit 6 is made at least in part of a textile material. Such a design is more consumer-oriented and user-friendly than the current, existing all plastic conduits, and will help to promote the usage of patient interface device 8 as, for example, a therapy device for sleep apnea. The advantages of such a textile-based delivery conduit 6 include a softer tactile feel and a greater visual appeal, both of which are expected to promote patient comfort and usage and therefore therapy compliance.

FIG. 2 is an isometric view of a textile-based delivery conduit 6A, which is one particular, exemplary embodiment of textile-based delivery conduit 6 of FIG. 1. As seen in FIG. 2, delivery conduit 6A includes a wall member 22 and a coil member 24 that is wrapped around and attached to the outer surface of wall member 22 and that gives structure and support to delivery conduit 6A.

FIG. 3 is an isometric view of wall member 22. As seen in FIG. 3, wall member 22, when expanded, has a tubular cross-section. In addition, wall member 22 is made at least partially of a textile material. The textile material of wall member 22 may be, for example and without limitation, nylon, a cotton polyester blend, or polyester. In the exemplary embodiment, wall member 22 is made entirely of a textile material wherein the textile material of wall member 22 is substantially impermeable to gas at pressures of 50 cm $H_2O$ and below (which are typical pressures that may be generated by pressure generating device 4 during therapy). As used herein, "substantially impermeable" shall mean that no more than 3% of the gas is able to leak thorough the textile material. This feature enables delivery conduit 6A (which, as seen in FIG. 2, includes several portions wherein wall member 22 is not covered by coil member 24 and thus is the only barrier to the gas) to effectively carry and deliver the pressurized gas generated by pressure generating device 4 without it leaking out through wall member 22 in anything more than negligible amounts.

In an alternative exemplary embodiment, wall member 22 is made of a textile material surrounded by a coating, such as, without limitation, silicone, urethane or thermoplastic elastomer (TPE), which provides gas impermeability functionality. In this alternative exemplary embodiment, the textile material of wall member 22 may not itself be substantially impermeable to gas at pressures of 50 cm $H_2O$ and below, but the provision of the coating makes wall member 22 substantially impermeable to gas at pressures of 50 cm $H_2O$ and below.

Furthermore, in the exemplary embodiment, coil member 24 is made of non-textile material, such as a plastic or metal, and is bonded to the exterior of wall member 22. As seen in FIG. 2, in the illustrated embodiment, coil member 24, when bonded to the exterior of wall member 22, has a helical shape. In addition, coil member 24 may have any of a number of different cross-sectional shapes. In the illustrated embodiment, coil member 24 has a cylindrical cross-section.

In addition, as noted above, in the embodiment shown in FIG. 2, coil member 24 is wrapped around the outer surface of wall member 22 helically in a right hand (RH) threading direction. Alternatively, coil member 24 may be wrapped around the outer surface of wall member 22 helically in a left hand (LH) threading direction. In addition, FIG. 2A shows a further alternative configuration for delivery conduit 6A, labeled 6A', wherein two coil members 24 are wrapped around the outer surface of wall member 22, one helically in a right hand (RH) threading direction and another helically in a left hand (LH) threading direction.

FIG. 4 is a cross-sectional view of coil member 24 (labeled 24A) according to one non-limiting particular exemplary embodiment. Coil member 24A in this embodiment is cylindrical in shape and is made of a plastic material capable of being wrapped around and bonded directly to the outer surface of wall member 22. The plastic material may be, for example and without limitation, a thermoplastic material such as polyethylene (PE), polypropylene (PP), polyester or nylon. In one embodiment, coil member 24A is wrapped around the outer surface of wall member 22 and heat set to the textile material of wall member 22 such that coil member 24A and wall member 22 will be fused together. In this embodiment, the heat setting/fusing is facilitated by making coil member 24A at least partly of a material that is also present in wall member 22. For example, if wall member 22 is made of nylon (or alternatively, polyester), coil member 24A may be made partially or wholly of nylon (or alternatively, polyester) to facilitate the heat setting/fusing. In this embodiment, the shared material that is included in coil member 24 acts as a bonding agent to ensure that the two components can be bonded together. In another embodiment, coil member 24A is bonded directly to the outer surface of wall member 22 by an appropriate separate bonding agent such as a suitable adhesive.

FIG. 5 is a cross-sectional view of coil member 24 (labeled 24B) according to an alternative non-limiting particular exemplary embodiment. Coil member 24B in this embodiment is cylindrical in shape and includes a cylindrical inner member 26 made of a plastic material such as, for example and without limitation, a thermoplastic material like polyethylene (PE), polypropylene (PP), polyester or nylon, surrounded and encased by an outer layer 28 made of a bonding agent which is structured to enable coil member 24 to be fixedly attached to wall member 22. In the exemplary embodiment, the bonding agent consists at least partly of a material that is also present in wall member 22 (e.g., without limitation, nylon or polyester) to facilitate heat setting/fusing between coil member 24 and wall member 22 as described above. In this embodiment, outer layer 28 acts as an adhesive mechanism that enables coil member 24B to be adhered to the outer surface of wall member 22.

FIG. 6 is a cross-sectional view of coil member 24 (labeled 24C) according to a further alternative non-limiting particular exemplary embodiment. Coil member 24C in this embodiment is cylindrical in shape and includes a cylindrical inner member 30 made of a metal material such as, for example and without limitation, steel or stainless steel, surrounded and encased by an outer layer 32 made of a bonding agent which is structured to enable coil member 24 to be fixedly attached to wall member 22. In the exemplary embodiment, the bonding agent consists at least partly of a material that is also present in wall member 22 (e.g., without limitation, nylon or polyester) to facilitate heat setting/fusing between coil member 24 and wall member 22 as described above. In this embodiment, outer layer 32 acts as an adhesive mechanism that enables coil member 24C to be adhered to the outer surface of wall member 22.

In one particular embodiment, delivery conduit 6A is made by first forming wall member 22. Wall member 22 may be, for example, formed from a flat sheet of textile material that is then formed into a tube shape. In this configuration, wall member 22 will have a seam running along the length thereof where opposite sides of the flat sheet have been attached to one another. Alternatively, wall member 22 may be formed directly into a tube shape using a circular knit (like a sock). In this configuration, wall member 22 will not have a seam running along the length thereof. Then, a cylindrically shaped support member (not shown) is inserted into the interior of wall member 22. The cylindrically shaped support member will have a diameter that is just slightly less than the internal diameter of wall member 22. With wall member 22 supported by the cylindrically shaped support member in this manner, coil member 24 (e.g., 24A, 24B, or 24C) is then wrapped around and bonded to the exterior surface of wall member 22. Wall member 22 having coil member bonded thereto and the cylindrically shaped support member are then separated from one another.

In an alternative particular embodiment, wall member 22 may be formed from a flat sheet of textile material by wrapping it around the cylindrically shaped support member and connecting (e.g., by adhering for fusing) opposite sides thereof to one another to form a tube structure (with or without the opposites sides overlapping one another). With wall member 22 supported by the cylindrically shaped support member in this manner, coil member 24 (e.g., 24A, 24B, or 24C) is then wrapped around and bonded to the exterior surface of wall member 22 as just described, wall member 22 having coil member bonded thereto and the cylindrically shaped support member are then separated from one another.

Figure 7:
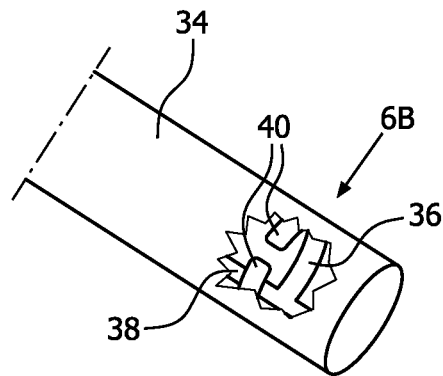
FIG. 7 is an isometric view of a textile-based delivery conduit of the system of FIG. 1 according to another particular, exemplary embodiment.

FIG. 7 is an isometric view in partial cut-away of a textile-based delivery conduit 6B, which is an alternative particular, exemplary embodiment of textile-based delivery conduit 6 of FIG. 1. As seen in FIG. 7, delivery conduit 6B includes a textile wall member 34 that surrounds and encases a skeleton frame member 36. Skeleton frame member 36 gives structure and support to delivery conduit 6B and prevents delivery conduit 6B from closing off completely when subjected to a moderate compression force (e.g., on the order of about 5 lbf to 10 lbf).

Figure 8:
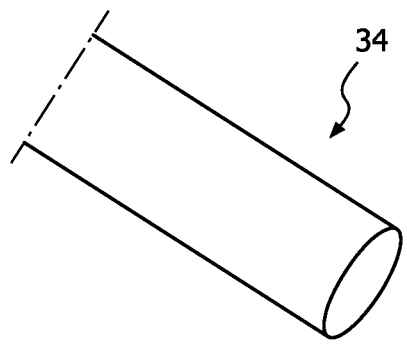
FIG. 8 is an isometric view of a textile wall member of the delivery conduit of FIG. 7.

FIG. 8 is an isometric view of wall member 34. As seen in FIG. 8, wall member 34, when expanded, has a tubular cross-section. In addition, wall member 34 is made of at least partially of a textile material such as, for example and without limitation, nylon, a cotton polyester blend, or polyester. In the exemplary embodiment, wall member 34 is made entirely of a textile material wherein the textile material of wall member 34 is substantially impermeable to gas at pressures of 50 cm $H_2O$ and below (which are typical pressures that may be generated by pressure generating device 4 during therapy). As with delivery conduit 6A, this feature enables delivery conduit 6B (which, like delivery conduit 6A, includes several portions wherein wall member 34 is not backed by skeleton frame member 36 and thus is the only barrier to the gas) to effectively carry and deliver the pressurized gas generated by pressure generating device 4 without it leaking out through wall member 34 in anything more than negligible amounts.

In an alternative exemplary embodiment, wall member 34 is made of a textile material surrounded by a coating, such as, without limitation, silicone, urethane or thermoplastic elastomer (TPE), which provides gas impermeability functionality. In this alternative exemplary embodiment, the textile material of wall member 34 may not itself be substantially impermeable to gas at pressures of 50 cm $H_2O$ and below, but the provision of the coating makes wall member 34 substantially impermeable to gas at pressures of 50 cm $H_2O$ and below.

Figure 9:
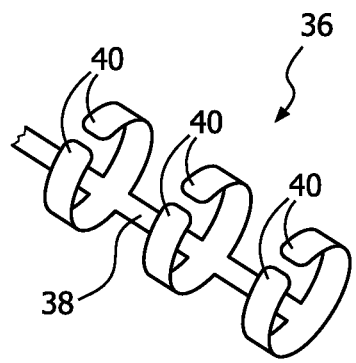
FIGS. 9-16 are isometric views of different embodiments of a skeleton frame member forming part of the delivery conduit of FIG. 7.

FIG. 9 is an isometric view of skeleton frame member 36 according to one particular embodiment. In the exemplary embodiment, skeleton frame member 36 is made of an injection molded thermoplastic plastic material such as, for example and without limitation, polyethylene (PE), polypropylene (PP), polyester or nylon. In particular implementations, the durometer of skeleton frame member 36 will be a function of the thickness and the specific material used. In an exemplary, non-limiting embodiment, the durometer of skeleton frame member 36 will range from 80 shore A (which is about 32 shore D) to 60 shore D. Alternatively, skeleton frame member 36 may be made of a metal material such as spring steel (medium to high carbon steel with high yield strength), or a metal or plastic material surrounded and encased by an outer layer (similar to outer layer 28 or 32) made of a bonding agent as described elsewhere herein to facilitate heat setting/fusing.

As seen in FIG. 9, in the illustrated embodiment, skeleton frame member 36 includes an elongated, linear spine member 38 which acts as a support backbone for skeleton frame member 36. Skeleton frame member 36 also includes a plurality of arcuate shaped rib members 40, wherein, as seen in FIG. 9, the rib members 40 are formed in a number of associated pairs located on and extending from opposite sides of spine member 38. In each such pair, the rib members 40 are located directly opposite one another such that each pair, along with spine member 38, forms an open C-shaped member.

As described above, wall member 34 surrounds and encases skeleton frame member 36. Wall member 34 may or may not be fixedly attached to skeleton frame member 36. In one exemplary embodiment, wall member 34 is bonded to skeleton frame member 36 using a suitable bonding agent. For example, wall member 34 may be initially formed from a flat sheet of textile material that is then wrapped around and bonded to skeleton frame member 36. In this embodiment, wall member 34 is made of a material that is flexible enough to allow it to stretch in the areas in between rib members 40 (i.e., in between the areas where it is attached to skeleton frame member 36). The bonding may be by way of heat setting/fusing as described elsewhere herein or by way of a suitable adhesive. In an alternative exemplary embodiment, wall member 34 is not fixedly attached to skeleton frame member 36. Such a configuration allows wall member 34 to bend easily and slide over the surface of skeleton frame member 36, promoting flexibility.

Figure 10:
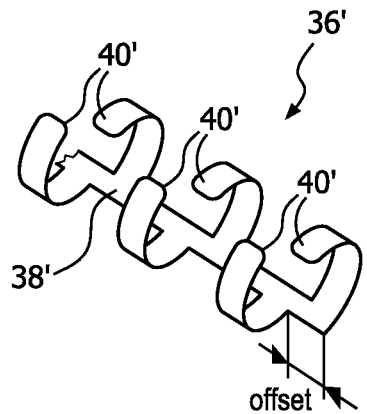

FIG. 10 is an isometric view of a skeleton frame member 36' according to an alternative particular embodiment. Skeleton frame member 36' may be substituted for skeleton frame member 36 in delivery conduit 6B and may be made of the same materials as skeleton frame member 36 (it may also have the example durometers described above). In this embodiment, skeleton frame member 36' includes an elongated, linear spine member 38' which acts as a support backbone for skeleton frame member 36'. Skeleton frame member 36' also includes a plurality of arcuate shaped rib members 40' located on and extending from opposite sides of spine member 38'. As seen in FIG. 10, the rib members 40' in this embodiment are arranged in a staggered configuration such that none of the rib members 40' is located directly opposite another rib member 40. In other words, immediately adjacent pairs of the rib members 40' located on opposite sides of spine member 38' are offset from one another (i.e., not directly opposite one another) along the length of spine member 38'.

Figure 11:
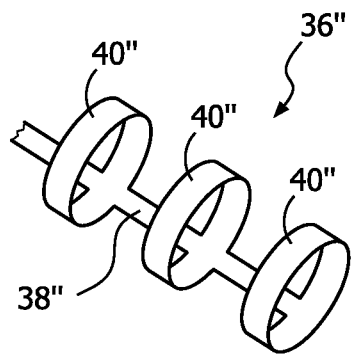

FIG. 11 is an isometric view of a skeleton frame member 36" according to another alternative particular embodiment. Skeleton frame member 36" may be substituted for skeleton frame member 36 in delivery conduit 6B and may be made of the same materials as skeleton frame member 36 (it may also have the example durometers described above). In this embodiment, skeleton frame member 36" includes an elongated, linear spine member 38" which acts as a support backbone for skeleton frame member 36". Skeleton frame member 36" also includes a plurality of rib members 40" that are spaced along spine member 38". In this embodiment, each rib member 40" is in the form of closed annular ring member extending from spine member 38".

Figure 12:
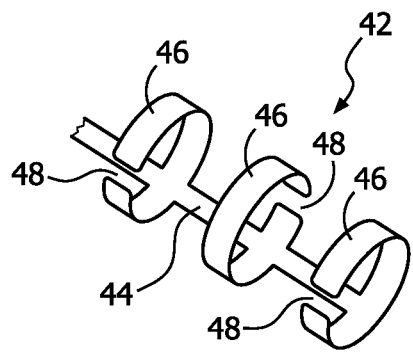

FIG. 12 is an isometric view of a skeleton frame member 42 according to a further alternative particular embodiment. Skeleton frame member 42 may be substituted for skeleton frame member 36 in delivery conduit 6B and may be made of the same materials as skeleton frame member 36 (it may also have the example durometers described above). In this embodiment, skeleton frame member 42 includes an elongated, linear spine member 44 which acts as a support backbone for skeleton frame member 42. Skeleton frame member 42 also includes a plurality of C-shaped rib members 46 located on and extending from spine member 44. Each of the C-shaped rib members 46 has a gap 48 provided therein. In this embodiment, C-shaped rib members 46 are positioned such that immediately adjacent C-shaped rib members 46 are offset from one another a certain amount, such as, without limitation, 180 degrees (i.e., the gaps 48 thereof are offset from one another by, for example, 180 degrees or some other suitable amount).

Figure 13:
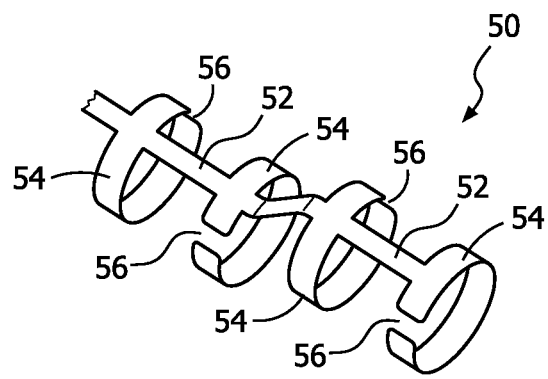

FIG. 13 is an isometric view of a skeleton frame member 50 according to still a further alternative particular embodiment. Skeleton frame member 50 may be substituted for skeleton frame member 36 in delivery conduit 6B and may be made of the same materials as skeleton frame member 36 (it may also have the example durometers described above). In this embodiment, skeleton frame member 50 includes an elongated, non-linear running spine member 52 (having position about the outer periphery of skeleton frame member 50 that changes along the length thereof) which acts as a support backbone for skeleton frame member 50. Skeleton frame member 50 also includes a plurality of C-shaped rib members 54 located on and extending from spine member 52. Each of the C-shaped rib members 54 has a gap 56 provided therein. In this embodiment, C-shaped rib members 54 are positioned such that immediately adjacent C-shaped rib members 54 are offset from one another a certain amount, such as, without limitation, 180 degrees (i.e., the gaps 56 thereof are offset from one another by, for example, 180 degrees or some other suitable amount).

Figure 14:
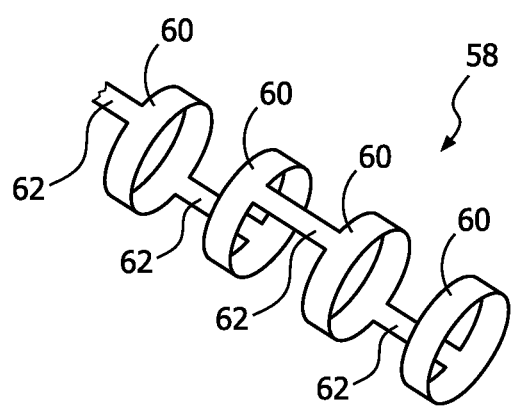

FIG. 14 is an isometric view of a skeleton frame member 58 according to yet another alternative particular embodiment. Skeleton frame member 58 may be substituted for skeleton frame member 36 in delivery conduit 6B and may be made of the same materials as skeleton frame member 36 (it may also have the example durometers described above). In this embodiment, skeleton frame member 58 includes a plurality of closed annular rib members 60 that are spaced along the length of skeleton frame member 58. In addition, each adjacent pair of rib members 60 is joined by a respective joining member 62. In the illustrated embodiment, immediately adjacent joining members 62 are offset 180 degrees from one another about the closed annular rib members 60 (i.e., as seen in FIG. 14, the joining members 62 alternate between being positioned on a top side of skeleton frame member 58 and a bottom side of skeleton frame member 58).

Figure 15:
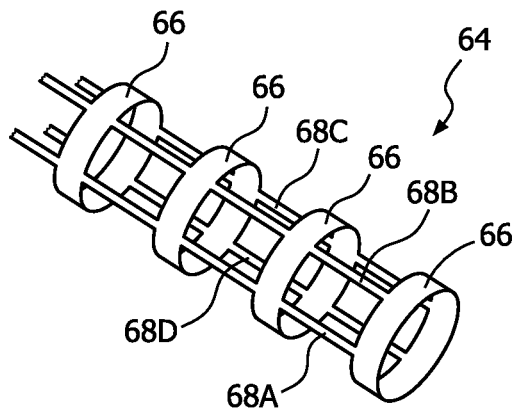

FIG. 15 is an isometric view of a skeleton frame member 64 according to still a further alternative particular embodiment. Skeleton frame member 64 may be substituted for skeleton frame member 36 in delivery conduit 6B and may be made of the same materials as skeleton frame member 36 (it may also have the example durometers described above). In this embodiment, skeleton frame member 64 includes a plurality of closed annular rib members 66 that are spaced along the length of skeleton frame member 64. In addition, each adjacent pair of rib members 66 is joined by a set of four linear joining members 68A, 68B, 68C, and 68D that each extend along the length of skeleton frame member 64.

Figure 16:
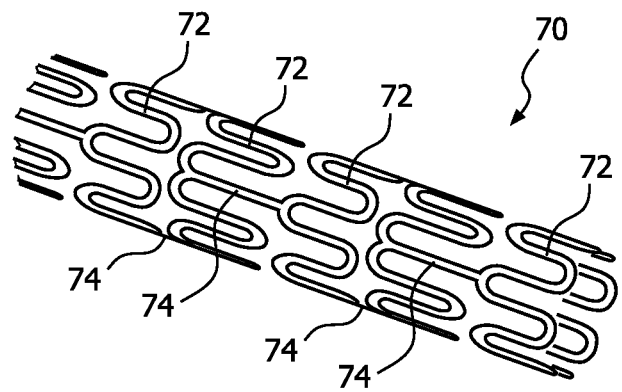

FIG. 16 is an isometric view of a skeleton frame member 70 according to yet another alternative particular embodiment. Skeleton frame member 70 may be substituted for skeleton frame member 36 in delivery conduit 6B and may be made of the same materials as skeleton frame member 36 (it may also have the example durometers described above). In this embodiment, skeleton frame member 70 includes a plurality of rib members 72 that are spaced along the length of skeleton frame member 70. As seen in FIG. 16, each rib member 72 has an oscillating, waveform-like structure (e.g., similar to a sine wave; other oscillating, waveform-like shapes, such as, without limitation, a square wave, a triangle wave or a sawtooth wave, are also possible). In addition, each adjacent pair of rib members 72 is joined by a respective one or more joining members 74. Skeleton frame member 70 has a shape similar to that of a known bioresorbable vascular stent sold by Abbott Laboratories under the name ABSORB™.

In the embodiments of FIGS. 10-16 just described, wall member 34 may or may not be fixedly attached to skeleton frame member 36', 36", 42, 50, 58, 64, 70 as described elsewhere herein.

In addition, it will be understood that the particular skeleton frame members 36', 36", 42, 50, 58, 64, 70 just described are meant to be exemplary, and that a skeleton frame member that resists collapse having other, different and/or more complex shapes may also be used within the scope of the present invention.

Figure 17:
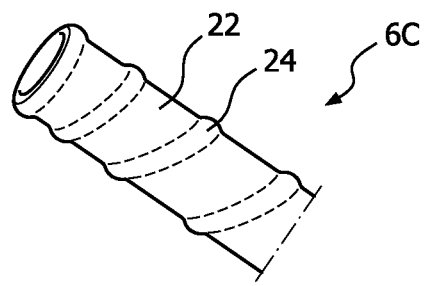
FIG. 17 is an isometric view of a textile-based delivery conduit of the system of FIG. 1 according to a further alternative particular, exemplary embodiment.

FIG. 17 is an isometric view of a textile-based delivery conduit 6C, which is another particular, exemplary embodiment of textile-based delivery conduit 6 of FIG. 1. Delivery conduit 6C is similar to delivery conduit 6A, and like components are labeled with like reference numerals. As seen in FIG. 17, delivery conduit 6C includes a wall member 22 as described in detail elsewhere herein as described in detail elsewhere herein, and a coil member 24, also as described in detail elsewhere herein in various embodiments (e.g., FIGS. 4-6). However, in delivery conduit 6C, wall member 22 surrounds and encases coil member 24. Coil member 24 thus gives structure and support to delivery conduit 6C and prevents delivery conduit 6C from closing off completely when subjected to a moderate compression force (e.g., on the order of about 5 lbf to 10 lbf). In addition, as described in connection with delivery conduit 6B, wall member 22 may or may not be fixedly attached to coil member 24.

In one particular implementation of delivery conduit 6A, 6A' 6B, or 6C, the outer diameter of wall member 22 or wall member 34, as the case may be, will be less than or equal to 30 mm, and the bend radius of delivery conduit 6A or 6B will be less than or equal to 50 mm. As used herein, the term "bend radius" shall mean the minimum radius, measured to the inside curvature, one can bend a pipe, tube, sheet, cable or hose without kinking it, damaging it, or shortening its life.

Moreover, a number of different embodiments of a delivery conduit (e.g., delivery conduits 6A, 6A' 6B, 6C) have been described in detail herein. For each of those embodiments, four different parameters and two different ratios calculated from the four parameters may be specified to define particular implementations that provide a very light weight, highly flexible fluid delivery device. Those four parameters are: (i) the outer diameter of the delivery conduit (e.g., in mm), (ii) the bend radius of the delivery conduit (e.g., in mm), (iii) the length of the delivery conduit (e.g., in mm), and (iv) the mass of the delivery conduit (e.g., in grams) In addition, the two ratios are: (i) a bend radius to outer diameter ratio, which, as used herein, shall mean the bend radius of the delivery conduit/outer diameter of the delivery conduit (in like units such as mm/mm), and (ii) a mass to length ratio, which, as used herein, shall mean the mass of the delivery conduit in grams/length of the delivery conduit in mm. In one particular embodiment, the outer diameter of the delivery conduit may range from 5 mm to 30 mm, the bend radius of the delivery conduit may range from 5 mm to 50 mm, the length of the delivery conduit is 330 mm, and the mass of the delivery conduit may range from 10 to 35 grams (or alternatively, 10 to 20 grams) In addition, in another particular embodiment, a delivery conduit (in the various embodiments described elsewhere herein, e.g., delivery conduit 6A, 6A' 6B, 6C) may be made to have a bend radius to outer diameter ratio that ranges from 1.00 to 1.67 and/or a mass to length ratio (in grams/mm) that ranges from 0.03 to 0.06.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A delivery conduit for delivering a flow of gas in a respiratory therapy system, comprising:
    an elongated wall member made of a textile material; and
    a support member extending along at least a portion of a length of the wall member and engaging an inner surface of the wall member, wherein the support member engages less than an entirety of the inner surface of the wall member such that a plurality of portions of the wall member are not engaged by the support member and at the plurality of portions the wall member is the only barrier to the gas within the delivery conduit, wherein the support member is a frame member provided within the wall member and engaging the inner surface of the wall member, the frame member including one or more joining members and a plurality of rib members coupled to at least one of the one or more joining members, wherein the one or more joining members comprise a spine member extending along a length of the support member, wherein the rib members have an arcuate shape and are formed in number of associated pairs located on and extending from opposite sides of the spine member, wherein in each of the associated pairs the rib members are located directly opposite one another, wherein in each of the associated pairs the rib members have a gap that separates a distal end of each of the rib members, and wherein in immediate adjacent ones of the associated pairs, the gaps thereof are offset from one another.

2. The delivery conduit according to claim 1, wherein the spine member is linear.

3. The delivery conduit according to claim 1, wherein the support member is made of a material having a durometer of 80 shore A to 60 shore D.

4. The delivery conduit according to claim 1, wherein the support member is made of a plastic material.

5. A delivery conduit for delivering a flow of gas in a respiratory therapy system, comprising:
    an elongated wall member made of a textile material; and
    a support member extending along at least a portion of a length of the wall member and engaging an inner surface of the wall member, wherein the support member engages less than an entirety of the inner surface of the wall member such that a plurality of portions of the wall member are not engaged by the support member and at the plurality of portions the wall member is the only barrier to the gas within the delivery conduit, wherein the support member is a frame member provided within the wall member and engaging the inner surface of the wall member, the frame member including one or more joining members and a plurality of rib members coupled to at least one of the one or more joining members, wherein the one or more joining members comprise a spine member extending along a length of the support member, and wherein the rib members have an arcuate shape and are formed in a number of associated pairs located on and extending from opposite sides of the spine member, wherein the rib members are arranged in an offset configuration such that in each of the associated pairs the rib members are not located directly opposite one another.

* * * * *